United States Patent [19]

Sand

[11] Patent Number: 5,374,265

[45] Date of Patent: Dec. 20, 1994

[54] COLLAGEN TREATMENT APPARATUS AND METHOD

[75] Inventor: Bruce J. Sand, Hidden Hills, Calif.

[73] Assignee: Laser Biotech, Inc., Los Angeles, Calif.

[21] Appl. No.: 926,331

[22] Filed: Aug. 6, 1992

Related U.S. Application Data

[63] Continuation of Ser. No. 546,252, Jun. 29, 1990, Pat. No. 5,137,530, which is a continuation-in-part of Ser. No. 374,958, Jun. 30, 1989, Pat. No. 4,976,709, which is a continuation-in-part of Ser. No. 285,379, Dec. 15, 1988, abandoned, which is a continuation of Ser. No. 170,070, Mar. 14, 1988, abandoned, and a continuation of Ser. No. 67,381, Jun. 24, 1987, abandoned, and a continuation of Ser. No. 914,169, Oct. 1, 1986, abandoned, which is a continuation-in-part of Ser. No. 781,225, Sep. 27, 1985, abandoned.

[51] Int. Cl.$^5$ .............................................. A61N 5/06
[52] U.S. Cl. ...................................................... 606/5
[58] Field of Search .......................... 128/6, 395–398; 372/41; 606/3–5, 13–16

[56] References Cited

U.S. PATENT DOCUMENTS

| | | | |
|---|---|---|---|
| 4,330,763 | 5/1982 | Esterowitz | 372/41 |
| 4,381,007 | 4/1983 | Doss . | |
| 4,391,275 | 7/1983 | Frankhauser et al. . | |
| 4,461,294 | 7/1984 | Baron | 606/5 |
| 4,537,193 | 8/1985 | Sand | 606/4 |
| 4,538,608 | 9/1985 | L'Esperance | 606/3 |
| 4,558,698 | 12/1985 | O'Dell | 128/395 |
| 4,580,559 | 4/1986 | L'Esperance | 128/395 |
| 4,665,913 | 5/1987 | L'Esperance | 606/3 |
| 4,669,466 | 6/1987 | L'Esperance | 606/3 |
| 4,799,478 | 1/1989 | Fedorov et al. | 128/303.1 |
| 4,884,884 | 12/1989 | Reis | 606/5 |
| 4,887,592 | 12/1989 | Loertscher | 606/5 |
| 4,907,585 | 3/1990 | Schachar | 606/28 |
| 4,907,586 | 3/1990 | Bille et al. | 606/5 |
| 4,907,587 | 3/1990 | Fedorov et al. | 606/28 |
| 4,931,053 | 6/1990 | L'Esperance | 606/4 |
| 5,152,759 | 10/1992 | Parel et al. | 606/5 |
| 5,263,951 | 11/1993 | Spears | 606/12 |

FOREIGN PATENT DOCUMENTS

| | | | |
|---|---|---|---|
| 3148748 | 7/1983 | Germany | 606/4 |
| 929097 | 1/1982 | U.S.S.R. . | |

OTHER PUBLICATIONS

Horn, "New Refractive Method for Laser Thermal Keratoplasty with the Co:MgF$_2$ Laser," J. Cataract Refract Surg., vol. 16, Sep. 1990, pp. 611–616.

Spears et al., "Corneal Refractive Correction by Laser Thermal Keratoplasty," Proceedings of Laser–Tissue Interaction, SPIE vol. 1202, Jan. 15–17, 1990, pp. 334–340.

Chandonnet et al., "Corneal Reshaping by Laser-Induced Thermokeratoplasty," LEOS '89, Lasers and Electro-Optics Society Annual Meeting Conference Proceedings, Oct. 17–20, 1989, IEEE Catalogue No. 89CH2641-0, pp. 457–458.

Cotliar et al., "Excimer Laser Radial Keratotomy," Ophthalmology, vol. 92, No. 2, Feb. 1985, pp. 206–207.

Mainster, "Ophthalmic Applications of Infrared Lasers—Thermal Considerations," vol. 18, No. 4, Apr. 1979, pp. 414–420.

Doss et al., "An Electrothermal Technique for the Alteration of Corneal Curvature," Los Alamos Scientific Laboratory, LA-7155-MS Informal Report, Feb. 1978, pp. 1–7.

Horn, "Laser Thermokeratoplasty Shows Promise," Ophthalmology, Jun. 1, 1989, pp. 29–30.

Wright, "Laser Thermokeratoplasty Shows Promise", Ophthalmology, pp. 1 and 30, (Jun. 1, 1989).

(List continued on next page.)

Primary Examiner—Max Hindenburg
Attorney, Agent, or Firm—Majestic, Parsons, Siebert & Hsue

[57] ABSTRACT

A method and apparatus for controlled thermal shrinkage of collagen tissue by irradiation with coherent energy in the wavelength band of 1.80 to 2.55 microns as generated by a laser. A specific application to ophthalmological corneal reshaping is described.

63 Claims, 3 Drawing Sheets

OTHER PUBLICATIONS

Householder, "Laser Induced Thermal Keratoplasty", *SPIE Laser Surgery: Advanced Characterization, Therapeutics and Systems*, vol. 1066, pp. 18–23 (1989) Jan.

Chetvertukhin et al. "Refractive Thermo– and Laser Keratoplasty", *Vestn. Oftal.*, pp. 67–69 (USSR 1982), and English Translation.

Bargeron et al., "Calculated and Measured Endothelial Temperature Histories of Excised Rabbit Corneas Exposed to Infrared Radiation", *Experimental Eye Research*, vol. 32, No. 2, pp. 241–250 (1981).

Stuck et al., "Ocular Effects of Holmium (2.06 $\mu$m) and Erbium (1.54 $\mu$m) Laser Radiation", *Health Physics*, vol. 40, pp. 835–846 (1981).

Stringer et al. "Shrinkage Temperature of Eye Collagen", *Nature*, vol. 204, No. 4965, p. 1307 (1964).

Horn, "A New Method For Refractive Correction Using Laser Thermokeratoplasty", orally presented at the 2nd American–International Congress on Cataract, IOL and Refractive Surgery, in Washington, D.C., (Apr. 25, 1989).

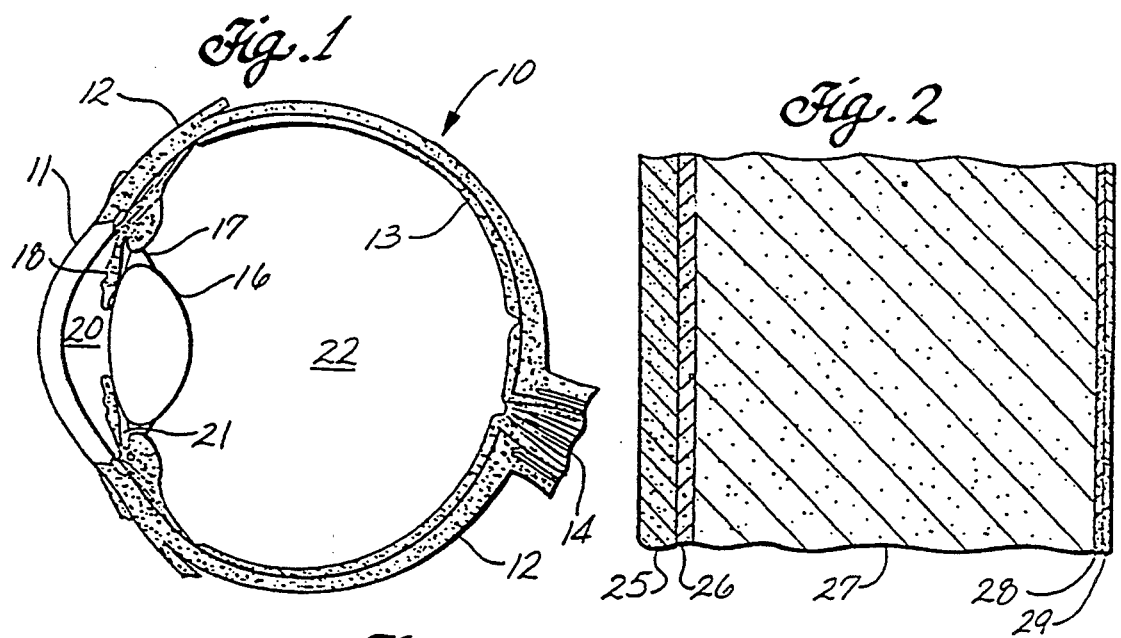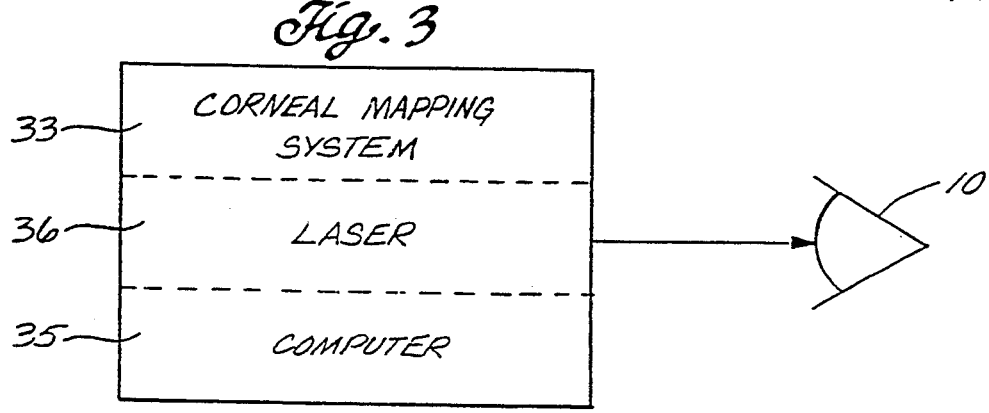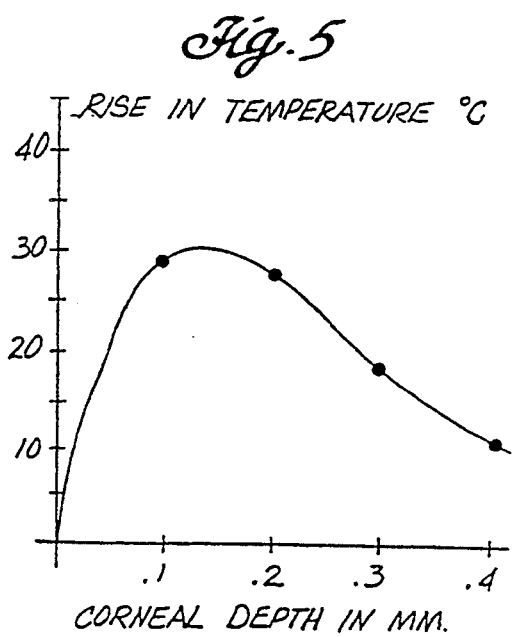

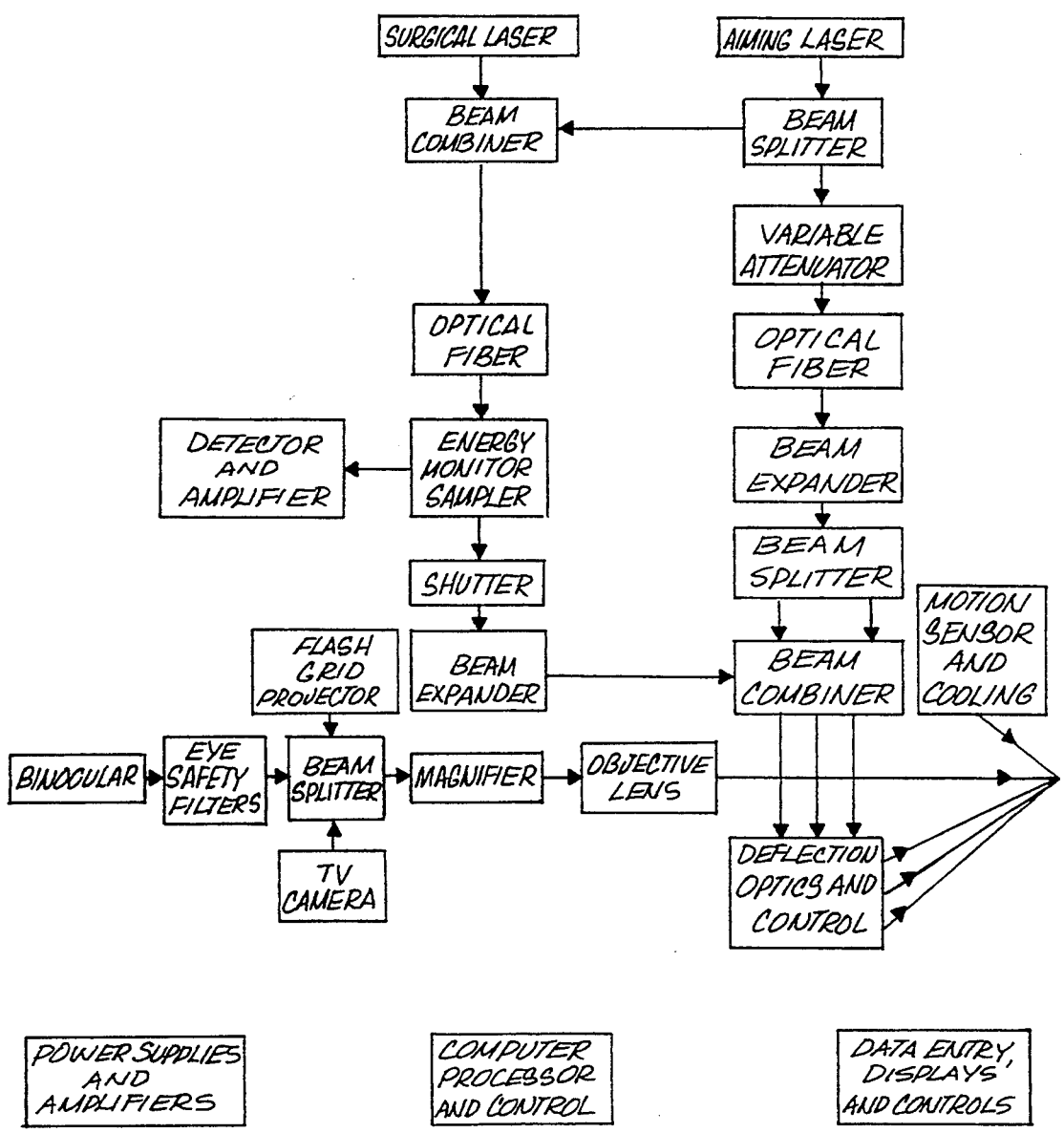

COLLAGEN TREATMENT APPARATUS AND METHOD

CROSS-REFERENCE TO RELATED APPLICATION

This is a continuation of application Ser. No. 07/546,252 (filed Jun. 29, 1990), now U.S. Pat. No. 5,137,530, which is a continuation-in-part of application Ser. No. 07/374,958 (Jun. 30, 1989) now U.S. Pat. No. 4,976,709 which is a continuation-in-part of application Ser. No. 07/285,379 (Dec. 15, 1988) abandoned which is a continuation of applications Ser. No. 07/170,070 (Mar. 14, 1988) abandoned, 07/067,381 (Jun. 24, 1987) abandoned, and 06/914,169 (Oct. 1, 1986) abandoned the latter being a continuation-in-part of application Ser. No. 06/781,225 (Sep. 27, 1985) abandoned.

BACKGROUND OF THE INVENTION

Collagen connective tissue is ubiquitous in the human body and demonstrates several unique characteristics not found in other tissues. It provides the cohesiveness and tenacity of the musculo-skeletal system, the structural integrity of the viscera, as well as the elasticity of the integument.

Most endothelial-lined structures of the body have collagen cores for specific functional purposes. Collagen cores are found in structures as diverse as the trabecular meshwork of the aqueous filtration system of the eye, and the valves of the heart. The walls of the great vessels share their collagen integrity with the ligamentous bony attachments and the tendinous or sinewy muscular attachments to the long bones. The cornea of the eye is a unique example of collagen connective tissue with the cornea stroma (accounting for about 90% of the total thickness of the cornea) demonstrating a high transparency of cross-oriented individual sheets or lamellae of collagen with a high (about 70%) water content and lesser (about 8%) amounts of protein and muco-polysaccharides.

Intermolecular cross-links provide collagen connective tissue with unique physical properties of high tensile strength and substantial elasticity. The extracellular matrix of this tissue consists of complex macromolecules, the biosynthesis of which involves several specific reactions that are often under stringent enzymatic control. The cross-linking is mediated, for example, by the copper-dependent enzyme lysyl-oxidase, and can be inhibited by chemicals such as B-aminoproprionitrile, as well as by various types of energy such as heat and photonic radiation. The net accumulation of collagen connective tissue is then dependent upon the precise balance between the synthesis and degradation of the connective tissue components.

A previously recognized property of hydro-thermal shrinkage of collagen fibers when elevated in temperature to the range 60° to 70° C. (an increase of about 30° C. above normal body temperature) is but one of the unique characteristics of this tissue not exhibited by other body tissues. Temperature elevation ruptures the collagen ultrastructural stabilizing cross-links, and results in immediate contraction in the fibers to about one-third of their original lineal dimension, while increasing the caliber of the individual fibers without changing the structural integrity of the connective tissue.

The present invention is directed to a method and apparatus for effecting controlled lineal contraction or shrinkage of collagen fibers to provide a multitude of nondestructive and beneficial structural changes and corrections within the body. The invention has application to the alteration of collagen connective tissue throughout the body, and will be described with specific reference to correction of refractive disorders of the cornea of the eye.

These applications have received some discussion in existing literature, but presently known techniques do not provide an adequate basis for effective use of this knowledge of the properties of collagen as a safe and predictable treatment method.

The cornea is a layered structure which provides the majority of the eye's refractive or focusing power for incoming light rays which are transmitted through the crystalline lens of the eye to light-sensitive receptors of the retina. The corneal layers, from outer to inner surfaces, include the epithelium, Bowman's membrane, a relatively thick central stroma formed of cross-oriented collagen ribbons or sheets, Descemet's membrane, and the endothelium. The as-yet unmet challenge is to achieve a thermal profile within the stroma to attain controlled, predictable collagen shrinkage and resulting corneal shape change and adjustment of refractive effects without damaging the adjacent layers.

An earlier approach to corneal reshaping to correct vision defects involved direct application of a heated probe to the corneal epithelium to transmit heat to the stromal collagen fibers. This technique, sometimes called thermokeratoplasty or TKP, was substantially unsuccessful in that peak temperatures were necessarily achieved in the outer corneal layers rather than in the stroma where the beneficial effect of collagen heating was desired. The most serious and discouraging problem was irreparable temperature damage to the corneal epithelium and its basement membrane, with consistent findings of thermal dissolution and persistent defects in this membrane. This has resulted in faulty epithelial adhesion and recurrent corneal epithelial erosions.

In contrast to corneal-stroma problems encountered in previous investigations, the desired method herein disclosed achieves highest shrinkage temperatures in the midstroma, and lowest in the region of Decemet's membrane and the endothelial monolayer on the inner surface of the cornea. The thermal profile must be controlled within a narrow peak range of 5° to 7° C. in order to destabilize the covalent bonding (or to disrupt interchain hydrogen bonds) of this triple-helical collagenous domain to achieve desired shrinkage, and without significantly traumatizing the keratocytes or denaturing the collagen fibrils. The thermal trauma associated with earlier efforts in this field leads to an acute inflammatory tissue response which results in the removal of denatured collagen, and is characterized by the deposition and subsequent cross-linking of newly elaborated collagen at the site as catalyzed by the enzyme lysyl oxidase.

The rapid replacement of contracted collagen fibers by new mature collagen following trauma results in the unwanted reversal of the desired corneal reconfiguration. In the absence of trauma, the half life of Type I collagen has been shown to be consistent with the life of the experimental animal.

Prior investigations, however, have not considered the importance of the atraumatic attainment of the proper thermal profile for protracted or permanent recurving of the cornea in the absence of collagen fibrillar replacement associated with trauma and the resulting inflammatory response.

Damage to the endothelial monolayer is the most disturbing problem encountered when the peak temperature is too far posterior in the cornea. Factors influencing the quality of this most important corneal layer include the absolute number of viable endothelial cells, and the morphology of these cells. Endothelial cells, unlike epithelial cells, are not replaced following trauma. There are several studies suggesting that cell shape (polymegathism and pleomorphism) is more closely related to the functional reserve of this layer than to endothelial cell density, but in either case complications will result in persistent edema, bullous keratopathy and loss of transparency of the cornea.

The problem of confining peak temperature to the stroma while maintaining acceptably lower temperatures in the inner and outer adjacent corneal layers is recognized in the prior art. U.S. Pat. No. 4,326,529 and 4,381,007, for example, disclose use of radio-frequency heating while irrigating the outer corneal surface with a cooling saline solution. Published reports on the technique, however, note ciliary spasm and fluctuating corneal power (topographic hysteresis) up to two months postoperatively. All patients had stroma scarring after the procedure, and the flattening induced was short lived.

The emergence of the laser as a practical tool for ophthalmologists has led to investigation of the use of coherent energy as a means for achieving corneal shape change to correct vision defects. One such application, essentially unrelated to the present invention, is disclosed in U.S. Pat. No. 4,461,294 which proposes the laser as a tissue-destructive (ablative photodecomposition) tool for forming radial corneal scars in a technique called radial keratotomy.

Use of the laser as a corneal collagen-shrinking tool has also been disclosed in the literature, but not in the context of a practical system which avoids tissue necrosis in the corneal epithelium, while providing predictable reconfiguration of the tissue without loss of transparency. The known technology thus does not disclose a procedure which avoids tissue necrosis, and produces protracted or permanent corneal recurving proportional to energy distribution, and repeatable (as indicated by animal studies) for similar exposure patterns and energy level.

The literature suggests that by properly selecting the absorption coefficient and using heat removal at the corneal surface, a proper temperature profile can be achieved in the cornea (high in the stroma and low in both the epithelium and endothelium). These studies conclude that the absorption coefficient must be in the range of 190 cm$^{-1}$ for this to occur; this restricts the range of wavelength interest to 2.6 or 3.9 microns; and that no lasers are commercially available at those wavelengths. This conclusion that the proper thermal profile is solely wavelength dependent is incomplete and has discouraged investigation in other wavelength domains. It is further believed that earlier investigations have incorrectly assumed that the absorption coefficient of corneal stroma is closely approximated by the absorption coefficient of water.

The present invention recognizes that in addition to absorption coefficient and anterior surface heat removal, the footprint of the energy with time significantly influences the temperature profile in the cornea. Specifically, by using pulsed or burst mode energy, a proper temperature profile has been obtained at much lower absorption coefficients (15-120 cm$^{-1}$), allowing use of lasers operating in the range of 1.80-2.55 micron wavelengths within today's technology. This method avoids the trauma of improper thermal profiles, and obtains proportional changes from at least 2 to 13 diopters in refractive power related to exposure pattern and energy density. This method has been shown to be repeatable in that similar changes in corneal curvature were observed for similar patterns and exposure levels. Significant induced effect has persisted throughout follow-up investigation, lending evidence that the half-life of corneal collagen was undisturbed.

SUMMARY OF THE INVENTION

This invention is directed to collagen connective tissue shrinkage by the use of laser coherent energy in the infrared wavelength range of about 1.80 to 2.55 microns, and preferably in the range of about 2.0 to 2.2 microns, as generated by a solid-state device such as holmium-doped yttrium-lithium-fluoride (YLF) or yttrium-aluminum-garnet (YAG) crystal laser. This type of laser is relatively compact and easy to operate, and is capable of generating energy optimally absorbed within collagen tissue based on the spectral-absorption coefficients of these wavelengths, without damage or destruction of adjacent tissue.

In an ophthalmological context, the invention relates to laser keratoplasty using a laser having the aforementioned characteristics for collagen shrinkage and consequent reshaping of the cornea for correction of vision errors or defects. Irradiation and resulting heating of the corneal stroma is preceded by measurement or mapping of the untreated cornea contours, and computation of the specific corneal regions to be heated to produce the desired corrective reshaping.

Timing of energy delivery to the corneal stroma is an important factor in achieving an intracorneal temperature profile which peaks in the generally central and anterior portion of the stroma, while limiting temperature increases to safe and nontraumatic levels in the corneal tissue layers anterior and posterior of the stroma. The energy should be delivered in less than one second, and preferably in about 100 milliseconds (pulse or burst modes) to position the peak temperature correctly within the stroma. These techniques enable the use of irradiating wavelengths in the 1.80-2.55 micron range with relatively low absorption coefficients in the general range of 15 to 120 cm$^{-1}$.

BRIEF DESCRIPTION OF THE DRAWINGS

FIG. 1 is a horizontal sectional view of an eye;

FIG. 2 is a schematic cross-sectional view of the cornea;

FIG. 3 is a block diagram of the apparatus of the invention;

FIG. 5 is a plot of temperature elevation within the cornea; and

FIG. 6 is a block diagram of an optical delivery system.

DETAILED DESCRIPTION OF THE PREFERRED EMBODIMENT

Figure 4:
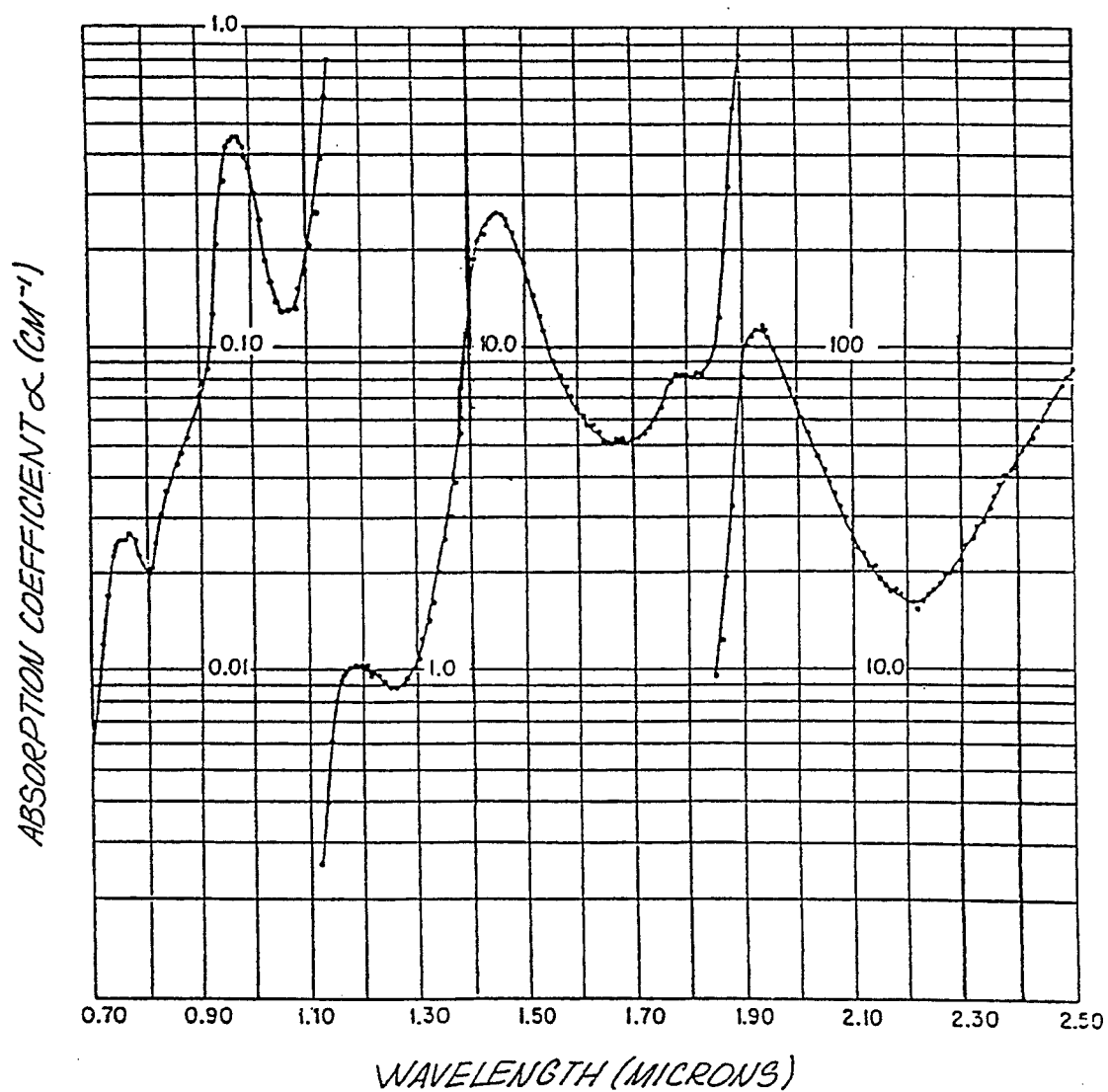
FIG. 4 is a plot of the absorption coefficient of distilled water as a function of incident wavelength.

The invention will be described in terms of a laser keratoplasty (LKP) system for shape modification of the human cornea, but the inventive principles are applicable to collagen shrinkage in other parts of the body. The LKP application is in a sense the most challenging use of the invention in view of the critical need to confine the heat field to target portions of the corneal stroma while avoiding excessive and potentially damaging temperature elevations in the sensitive tissues adjacent the stroma.

As a quick review of the anatomy of the eye, FIG. 1 is a horizontal section of an eye 10 having a roughly spherical structure with a transparent cornea 11 at the forward central portion, the remainder of the sphere of the "eyeball" being white and opaque sclera 12 which is attached to and blends with the periphery of the cornea. The eye's light-sensitive retina 13 extends along the rear and part of the forward inner surface of the sclera, and is connected to an optic nerve 14 which extends to the brain.

Positioned behind the cornea is a crystalline lens 16 supported by zonular ligaments 17, and the lens is capable of shape changes which enable the eye to focus on objects at various ranges. The eye's iris 18 is positioned between the cornea and lens to divide the space forward of the lens into an anterior chamber 20 and posterior chamber 21 which are filled with a clear and watery fluid called aqueous humor. The space behind the lens is filled with a clear gel-like body 22 called vitreous humor.

FIG. 2 is an enlarged schematic representation of the corneal cross-section to show the various layers of the cornea as already briefly discussed. The outermost or anterior layer is the epithelium 25 (typically about 50 microns thick and accounting for about ten percent of total corneal thickness) and its underlying basement membrane. The next layer is Bowman's membrane 26 (about 10-13 microns thick in the human eye) which is nonregenerative. The main body (about 90 percent of the total thickness) of the cornea is stroma 27 composed of clear sheets of collagenous material. The stroma is backed by Descemet's membrane 28 (about 5-10 microns thick), and the innermost or posterior layer is endothelium 29 which is a single layer of nonreproducing flattened cells of about 4-5 microns thickness.

The geometry of the cornea is complex, but has surfaces which are approximately concentric and spherical, the radius of curvature of the outer or anterior surface typically being about 8 millimeters. This value is smaller than the average radius of curvature of the sclera, giving the cornea a bulged appearance with respect to the sclera. The corneal diameter (greatest chord) is about 11 mm, and total thickness at the corneal center is about 0.55 mm.

From the structural standpoint, the characteristics of the cornea can be determined and predicted by an analytical model embodying the following corneal qualities:

a. The cornea is a thin dome-shaped shell supported peripherally by the sclera, and internally by uniformly distributed fluid pressure of the aqueous humor in the anterior chamber.

b. Zones or portions of the corneal shell which are heated to above about 60° C. will predictably shrink as the collagen lamellae of the stroma contract to about 30% of original length.

c. It is theorized that the corneal shell is sufficiently elastic to permit the fluid-pressure-supported posterior surface to retain substantially its original contour, and to force shrinkage-induced contour changes to occur primarily at the anterior surface where the refractive correction is of greatest effect. This effect is aided by confining shrinkage-producing stromal temperature elevations to the anterior part of the collagenous stroma.

About three-fourths of the eye's refractive power is determined by corneal curvature, and shape modification of this element of the eye's optical system thus provides a powerful tool in correction of refractive errors. Increasing the radius of curvature of the cornea will correct myopia (nearsightedness), and reduction of this parameter will correct hypermetropia (farsightedness). A properly patterned application of corneal shrinkage energy is also effective in correcting astigmatic errors.

To correct visual defects by laser keratoplasty, it is first necessary to measure existing vision and corneal shape or topography using a commercially available corneal mapping system 33 (FIG. 3) for contour determination along the meridians of the eye. This information forms the basis for instructions generated by a computer 35 (based on the corneal shell characteristics discussed above) as to the zones of the cornea which should undergo shrinkage to effect a change in the refractive power of the cornea for correction of defects. The remaining task is to achieve the desired temperature elevation in a controlled and safe fashion.

The laser is a useful tool in medicine for applying controlled and focused radiant energy for localized heating of tissue, and widely used in ophthalmology (e.g., for retinal repairs), and other specializations such as gynecology and otolaryngology. Depending on the use, these instruments may emit coherent energy in the visible-light band or may operate in the infrared or ultraviolet portions of the electromagnetic spectrum. These applications, however, are nearly all directed to photocoagulation, incision, perforation, or other tissue-destructive processes.

In the present invention, the desire is to heat selected areas of collagen tissue to shrinkage levels, but without damage or destruction of either the target or surrounding tissues. Preferably, the optical-delivery-system laser is integrated with the corneal mapping or topography system to enable computer control of laser output, as well as real-time or near-real-time monitoring of progressive corneal reconfiguration.

The conversion of coherent radiant energy to temperature elevation of a target is largely dependent on a physical parameter of the target tissue body called the optical absorption coefficient, which is a variable dependent on wavelength. It has previously been proposed (see, e.g., Mainster, Martin A., "Ophthalmic Applications of Infrared Lasers—Thermal Considerations," J. Invest. Ophthalmology 1979; 18:414) that the absorption coefficient of corneal collagen in the near infrared is approximated by that of water. The wavelength dependency of this variable has been previously disclosed, and FIG. 4 is a textbook graph plotting absorption coefficient (water) against wavelength.

My research, based in part on a finding that the absorption coefficient of collagen does not accurately correspond to that of water, has established the feasibility of using lasers which emit wavelengths in the range of about 1.80 to 2.55 microns where the collagen absorption coefficient is in the range of about 15 cm$^{-1}$ to about 120 cm$^{-1}$. Wavelengths corresponding to lower absorption coefficients may produce insufficient mid-stromal heating. Wavelengths corresponding to significantly higher absorption coefficients tend to move the peak of the temperature profile forwardly, creating a risk of epithelial damage.

Preferably, coherent radiation with wavelengths in the range of about 2.0 to 2.2 microns is used. Coherent radiation can be generated in this wavelength by a solid-state laser 36 using holmium-doped YAG or YLF crystals as mentioned above. These lasers are mechanically and optically relatively simple and easy to operate.

These solid-state lasers are believed to be superior to previously proposed gas lasers such as argon, krypton, HCl, and frequency-doubled CO systems. Argon and krypton lasers do not generate needed power levels. The HCl gas laser is a large laboratory instrument requiring large amounts of consumable gasses and major subsystems to create high flow rates under vacuum conditions and to chemically scrub the volatile gas reaction products. The frequency-doubled CO laser is large, and it is uncertain whether a suitable nonlinear crystal for frequency doubling at the required power level can be developed.

The research underlying this invention includes experiments with human corneal collagen tissue irradiated with pulses of about 0.10 second duration by a laser operating at about 2.1 microns at an energy level of about 0.5 joule. The predicted stromal collagen shrinkage occurred without loss of corneal transparency, and without damage to the epithelium, Bowman's membrane, or the strata underlying the corneal stroma.

Protection of the corneal layers anterior to the stroma is afforded by a slightly lower surface temperature, and by the normal tear layer on the epithelium. This protection can be increased by flowing either inert gas or liquid over the cornea during irradiation. Another technique for conducting heat from the corneal surface is to apply a contact lens "window" of a material such as sapphire which has high thermal conductivity and thermal mass.

FIG. 5 shows the computed temperature profile through the corneal thickness using a 2.1 micron solid-state laser irradiating a circular corneal area having a radius of about 1.5 mm for 0.1 seconds with about 0.5 joule of energy incident on the cornea, and using flowing-irrigant cooling of the corneal surface. The significant feature is that desired peak temperatures are confined to the anterior stroma (just forward of the cross-sectional centerline of the stroma) as shown in FIG. 5, and the adjacent corneal layers are not heated sufficiently to present a risk of tissue damage.

A key objective is to achieve a shrinkage-producing temperature elevation of at least 23° C. in the stroma, while preventing destructive temperature increases in the corneal epithelium and endothelium, and preserving corneal transparency. This goal is achieved by use of the recommended coherent wavelengths (and associated absorption coefficients) at moderate energy densities in a range up to about 100 joules per square centimeter, and relatively short-duration energy pulses (burst or pulse mode, or gated c-w) with a width in the range of 0.010 to less than 1.0 seconds, and preferably about 100 milliseconds. Preferably, a higher-power shorter-duration pulse is used (rather than a low-power long-duration exposure) to achieve the necessary temperature elevation with minimum thermal losses within the eye, and delivery of lower total energy to the eye.

A very short high-energy pulse presents a risk of excessive epithelial heating because there is insufficient time for the heat-removal mechanisms mentioned above (for example, a puff of cooling gas) to act. A long-duration pulse, on the other hand, leads to excessive conductive dissipation of heat within the stroma and away from the target shrinkage volume. A presently preferred "exposure time" for delivery of energy is 100 milliseconds for each element or spot in a shrinkage pattern.

Experimental efforts conducted to date have involved application of temperature-elevating energy to specific spaced-apart stromal zones in a series of dots which are small circles in the range of about 0.25 to 2.0 mm in diameter. The patterning of these dots depends on the kind of refractive correction which is needed. For example, a pattern of dotted radial spokes extending from an untreated central circular part of the cornea is effective in correction of myopia. A dotted circular pattern centered on the corneal axis is used for correction of farsightedness. One or more dotted linear arrays on a meridian is used for astigmatic corrections. These patterns do not involve application of shrinkage energy to the visual axis of the eye.

The treatment method is not limited to application of shrinkage heating in a "stitched" pattern of circular dots. For example, if energy is applied in a series of time-separated dots, the individual dots need not be circular, and a rectangular or other dot shape may be used to achieve a desired shrinkage effect. It is also optically possible to apply the shrinkage energy as a narrow line, or as a pattern of lines forming a rectangle or other shape. Thus, for example, a single application of heating energy can be in a circular or toroidal pattern.

In planning specific treatment programs, it is useful to consider energy density in determining the pattern of shrinkage radiation. Experimental results indicate that energy densities up to about 100 joules per square centimeter are consistent with establishing a desired temperature profile within the stroma, while preventing excessive heating in the tissue layers adjoining the stroma. Depending on the selected energy pattern, the applied energy per "shot" is typically in the range of about 0.01 to 5.0 joules.

It is also within the scope of this invention apply multiple shots of temperature-elevating energy each stromal zone in which shrinkage is to be effected. This can in some cases provide more accurate control of the profile of temperature increase within the stroma. For example, two or three energy pulses (each of about five to ten milliseconds duration) may be applied to a single zone, with short-duration interpulse separation of about 50 to 200 milliseconds.

This invention achieves controlled intrastromal shrinkage without causing thermal trauma and collagen coagulation, and a resulting unwanted inflammatory tissue response. Avoidance of the inflammatory response (a problem characteristic of prior-art investigations) is an important factor in achieving a long-duration chronic shape change of the cornea for correction of visual defects.

The overall system may take different forms, and one arrangement is shown in FIG. 6 which illustrates in block-diagram form an optical delivery system which includes a low-power aiming laser, a means for sensing unwanted eye movement, and the various associated controls and displays. Measurement of the refractive properties of the cornea before, during and after treatment is made by a corneal topography measuring device. One suitable such device identified as a "Corneal Analysis System," is marketed by EyeSys Laboratories, Houston, Tex.

Corneal measurement systems of this type typically make available a color CRT screen display of contour data, as well as printout of the corresponding information. These systems identify the astigmatic axis and permit selection of desired meridians of the cornea, and present in digital and false-color display either refractive power in diopters or radius of curvature (typically in millimeters). Data-acquisition optics are preferably positioned on the slitlamp base of the laser optical delivery system, with a working distance of about three inches from the corneal surface.

These systems typically have adjustable measurement fields (e.g., 0.8 mm to 7 mm, with a 42.5 diopter sphere), and achieve a resolution of about plus-or-minus one-quarter diopter over the full selected field. Data-processing time is rapid (in the range of twenty seconds from measurement to printout or screen display) and nearly real time, and image-subtraction routines enable rapid calculation and display of corneal-healing refractive change by comparing pre- and post-application images. This noncontacting measuring system does not effect corneal surface integrity, and the convex-mirror quality of the cornea is undisturbed as required for the image-subtraction, technique and other post-energy-application measurements.

Laser thermal keratoplasty using the laser exposure parameters discussed above provides an optimal thermal profile in the anterior and midstroma of the cornea for collagen fibrillar contraction. This profile is defined as 25° C. to 30° C. above the normal physiologic temperature, while maintaining substantially physiologic temperature in the epithelium and endothelium.

Collagen is considered to be metabolically inert in its steady state, and while thermally induced contraction occurs by the process of this invention, temperature elevations are below the thermal traumatic or inflammatory thresholds. In the absence of trauma, the dimensional collagen reconfiguration is believed to exhibit long-term stability.

The type-I collagen molecule consists of chains of 300-nm triple helixes joined by 67-nm uncoiled bonds. Controlled contractions of the individual fibrillar molecules require an exposure pattern consistent with magnitude and radial arc modifications desired.

An increase in the radius of curvature of the cornea results in the effective shortening of the focal length of the visual system of the eye, while a decrease in the radius or steepening of the cornea increases the focal length. A correction of myopia requires an increase of the radius, while hypermetropia is treated by decreasing the corneal radius of curvature. Corneal astigmatism is modified by flattening in the myopic meridian, while an opposite effect occurs at right angles to this recurvature.

This thermal keratoplasty process, therefore, requires not only an optimal thermal profile in the sagittal dimension, but to be effective in the modification of refractive error, also requires an exposure pattern in the plane of the corneal surface consistent with the desired magnitude and direction of radial arc changes. Studies on experimental animals have identified several exposure patterns resulting in corneal curvature modifications for myopic, hypermetropic, and astigmatic errors.

A 2-3 mm central laser exposure spot in the visual axis results in a maximal flattening of the corneal radius of curvature of from 0.5 to 18 diopters, depending upon energy level and exposure duration. A transient stromal haze occurs, but fades within 48 hours following energy application.

In order to avoid exposure in the visual axis, two additional effective flattening patterns have been identified. Each of these patterns or arrays spare the 3-mm central optical zone.

One array utilizes a symmetrical radial pattern of six to eight lines each comprising about six individual 0.5-mm spots spaced about 0.5-mm apart. Ten diopters of flattening has been obtained with this pattern.

Another, and perhaps most desired pattern, is the circumferential distribution of individual 0.5-mm exposures, sparing the 3-mm central optical zone. No haze is experienced and up to 15 diopters of myopic correction has been obtained with a multipulsed laser. The resulting refractive correction has persisted throughout an observation period exceeding 18 months. Since an inflammatory tissue response does not occur, it is likely that the reconfiguration is of protracted duration, and perhaps permanent.

Steepening occurs over a large range of corrections as the ring or circumferential pattern encroaches upon the peripheral cornea beyond 5 mm from the visual axis. Similar long-term duration is obtained.

Meridional modification is obtained by parallel lines 3-mm apart, and above and below the central optical zone in the direction of the meridian, each line utilizing 5 or 6 individual 0.5 mm exposure spots.

There has been described a new and effective system for irradiation of collagen tissue to produce corrective shape changes by controlled and predictable collagen shrinkage. While disclosed as a corneal shape-modifying technique, the system has application to other collagenous bodies, and is believed useful in fields ranging from cosmetic surgery to correction of defective heart valves or musculoskeletal injuries.

What is claimed is:

1. A keratoplasty system, comprising:
    a surgical laser that generates a first radiation beam within a wavelength range of about 1.80 to 2.55 microns,
    an aiming laser that generates a second radiation beam,
    a substantially transparent heat sink especially adapted to be positionable in contact with the surface of a cornea,
    means receiving said first and second radiation beams for directing them through said heat sink toward said corneal surface in a controlled pattern of a plurality of dots, and
    means for allowing binocular viewing of the cornea.

2. The system according to claim 1 wherein said directing means includes means for causing said pattern of a plurality of dots to be substantially circular.

3. A method of reshaping the curvature of a cornea, comprising the steps of:
    providing a source of infrared radiation within a wavelength range of 1.80 to 2.55 microns, and
    exposing at least one zone of an outside surface of the cornea to said radiation in a manner to raise the temperature of collagen tissue within a corneal stroma sufficient to shrink collagen tissue therein but without causing any substantial damage to either a corneal epithelium layer or corneal strata that underlie the stroma,
    whereby the shrinkage of said collagen causes the reshaping of the cornea.

4. The method according to claim 3 wherein the radiation providing step includes the step of using a laser as the source of the radiation.

5. The method according to claim 3 wherein the radiation exposing step includes the step of creating a temperature profile through the cornea at said at least one zone that has a maximum temperature in an anterior portion of the stroma.

6. The method according to claim 5 wherein said maximum temperature is caused to be in excess of about 60° C.

7. The method according to claim 6 wherein said exposing step is additionally accomplished without destruction or substantial damage to collagen tissue within the stroma.

8. The method according to claim 3 wherein the radiation exposing step includes the step of directing a sequence pulses of said radiation to the outside cornea surface.

9. The method according to claim 8 which comprises the additional step of measuring refractive properties of the cornea before, during and after the radiation pulse exposing step.

10. The method according to claim 3 wherein the radiation exposing step includes the step of directing said radiation against a plurality of zones across the outside cornea surface.

11. The method according to claim 10 wherein the infrared radiation source providing step includes providing a source of radiation within a wavelength range of from 2.0 to 2.2 microns.

12. The method according to claim 3, comprising an additional step of positioning an optically transparent heat sink in contact with the outside surface of the cornea.

13. The method according to claim 12 wherein the heat sink positioning step includes the step of positioning sapphire against the outside surface of the cornea.

14. The method according to claim 12 wherein the infrared radiation source providing step includes providing a source of radiation within a wavelength range of from 2.0 to 2.2 microns.

15. The method according to claim 3 wherein the step of exposing a plurality of zones of the cornea outside surface to radiation includes directing radiation against the cornea in a pattern of dotted radial spokes extending outward from an untreated central circular part of the cornea.

16. The method according to claim 3 wherein the step of exposing a plurality of zones of the cornea outside surface to radiation includes directing radiation against the cornea in a dotted circular pattern centered on an axis of the cornea.

17. The method according to claim 3 wherein the step of exposing a plurality of zones of the cornea outside surface to radiation includes directing radiation against the cornea in a dotted linear array on a meridian of the cornea.

18. The method according to claim 3 wherein the infrared radiation source providing step includes providing a source of radiation within a wavelength range of from 2.0 to 2.2 microns.

19. The method according to claim 5 wherein the infrared radiation source providing step includes providing a source of radiation within a wavelength range of from 2.0 to 2.2 microns.

20. A method of modifying the curvature of a cornea, comprising the steps of:

providing a source of infrared radiation within a wavelength range having corneal collagen absorption coefficients substantially only within a range of about 15 cm$^{-1}$ to 120 cm$^{-1}$, exposing at least one zone of an outside surface of the cornea to said radiation in a manner to raise the temperature of collagen tissue within a corneal stroma sufficient to shrink collagen tissue therein but without causing any substantial damage to a corneal strata that underlies the stroma, whereby the shrinkage of said collagen causes the curvature of the cornea to be modified.

21. The method according to claim 20 wherein the radiation exposing step includes using a laser as the source of the radiation.

22. The method according to claim 20 wherein the radiation exposing step includes the step of creating a temperature profile through the cornea at said at least one zone that has a maximum temperature in an anterior portion of the stroma.

23. The method according to claim 22 wherein said maximum temperature is caused to be in excess of about 60° C.

24. The method according to claim 23 wherein said radiation exposing step is additionally accomplished without destruction or substantial damage to collagen tissue within the stroma.

25. The method according to claim 20 wherein the radiation exposing step includes the step of directing a sequence pulses of said radiation to the outside cornea surface.

26. The method according to claim 25 which comprises the additional step of measuring refractive properties of the cornea before, during and after the radiation pulse exposing step.

27. The method according to claim 20 wherein the radiation exposing step includes the step of directing said radiation against a plurality of zones across the outside cornea surface.

28. The method according to claim 27 wherein the step of directing said radiation against plurality of zones includes the step of causing said zones to include a plurality of dots arranged in a curved path.

29. The method according to claim 27 wherein the step of directing said radiation against plurality of zones includes the step of causing said zones to include a plurality of dots arranged in a circle with a center substantially at an axis of the cornea.

30. The method according to claim 29 comprising an additional step of positioning an optically transparent heat sink in contact with the outside surface of the cornea.

31. The method according to claim 27 wherein the step of exposing a plurality of zones of the cornea outside surface to radiation includes directing radiation against the cornea in a pattern of dotted radial spokes extending outward from an untreated central circular part of the cornea.

32. The method according to claim 27 wherein the step of exposing a plurality of zones of the cornea outside surface to radiation includes directing radiation against the cornea in a dotted linear array on a meridian of the cornea.

33. The method according to claim 20 comprising an additional step of positioning an optically transparent heat sink in contact with the outside surface of the cornea.

34. The method according to claim 20 wherein the radiation exposing step includes directing radiation against the cornea in the shape of at least one dot having a diameter substantially within a range of 0.25 mm. to 2.0 mm.

35. The method according to claim 20 which comprises the additional steps of measuring refractive properties of the cornea before and after the exposing step.

36. The method according to claim 20 wherein the exposing step includes exposing said zone to said radiation in a manner to raise the temperature of collagen tissue within a corneal stroma sufficient to shrink collagen tissue therein but without causing any substantial damage to a corneal epithelium layer.

37. Apparatus for modifying a shape of a cornea, comprising:
   a source of radiation having a wavelength within a range of 1.80 to 2.55 microns,
   means transparent to said radiation for contacting an outer surface of a human cornea in order to conduct heat from said surface, and
   a system delivering said radiation through said contacting means with enough energy to raise a temperature of tissue within the cornea sufficient to modify the shape of the cornea.

38. Apparatus according to claim 37 wherein the radiation delivering system is characterized by delivering said radiation through said contacting means in a controlled pattern.

39. Apparatus according to claim 38 wherein said controlled pattern includes a plurality of dots.

40. Apparatus according to claim 39 wherein the radiation delivering system is further characterized by delivering said plurality of dots sequentially in time.

41. Apparatus according to claim 39 wherein the individual dots are circles having a diameter substantially within a range of 0.25 mm. to 2.0 mm.

42. Apparatus according to claim 38 wherein said controlled pattern includes a plurality of dots arranged in a circular pattern.

43. Apparatus according to claim 38 wherein said controlled pattern includes a plurality of dots arranged in at least one linear array.

44. Apparatus according to claim 38 wherein said controlled pattern includes one or more lines.

45. Apparatus according to claim 38 which additionally comprises an aiming laser positioned with a visible beam therefrom directed through said contacting means according to said controlled pattern, whereby the location of the pattern from the radiation source is made visible.

46. Apparatus according to claim 45 wherein the radiation source is a laser.

47. Apparatus according to claim 37 wherein the radiation source is characterized by emitting said radiation in a series of pulses.

48. Apparatus according to claim 37 wherein the radiation source is a laser.

49. Apparatus according to claim 37 wherein the radiation source has a wavelength within a range of 2.0 to 2.2 microns.

50. Apparatus according to claim 37 which additionally comprises means for measuring a shape of the cornea.

51. Apparatus according to claim 50 which additionally comprises computer means responsive to the measuring means for controlling a distribution of radiation by the radiation delivering means.

52. Apparatus according to claim 51 wherein the radiation source has a wavelength within a range of 2.0 to 2.2 microns.

53. Apparatus according to claim 37 wherein said contacting means includes a contact lens window.

54. Apparatus according to claim 53 wherein the radiation source has a wavelength within a range of 2.0 to 2.2 microns.

55. Apparatus according to claim 37 wherein said delivering system includes an optical fiber.

56. A keratoplasty system, comprising:
   a surgical laser that generates a first radiation beam having a wavelength range corresponding to a range of corneal collagen absorption coefficients of about 15 $cm^{-1}$ to about 120 $cm^{-1}$,
   an aiming laser that generates a second radiation beam,
   a substantially transparent heat sink especially adapted to be positionable in contact with the surface of a cornea,
   means receiving said first and second radiation beams for directing them through said heat sink toward said corneal surface in a controlled pattern of a plurality of dots, and
   means for allowing binocular viewing of the cornea.

57. Apparatus for modifying a shape of a cornea, comprising:
   a source of radiation having a wavelength range corresponding to a range of corneal collagen absorption coefficients of about 15 $cm^{-1}$ to about 120 $cm^{-1}$,
   means transparent to said radiation for contacting an outer surface of a human cornea in order to conduct heat from said surface, and
   a system delivering said radiation through said contacting means with enough energy to raise a temperature of tissue within the cornea sufficient to modify the shape of the cornea.

58. Apparatus according to claim 57 wherein the radiation source is characterized by emitting said radiation in a series of pulses.

59. Apparatus according to claim 57 wherein the radiation source is a laser.

60. Apparatus according to claim 57 wherein the radiation delivering system is characterized by delivering said radiation through said contacting means in a controlled pattern.

61. Apparatus according to claim 60 wherein said controlled pattern includes a plurality of dots.

62. Apparatus according to claim 60 which additionally comprises an aiming laser positioned with a visible beam therefrom directed through said contacting means according to said controlled pattern, whereby the location of the pattern from the radiation source is made visible.

63. Apparatus according to claim 62 wherein the radiation source is a laser.

* * * * *